United States Patent [19]
Greenberg

[11] Patent Number: 5,260,279
[45] Date of Patent: Nov. 9, 1993

[54] ENTERAL NUTRITION AND MEDICAL FOODS HAVING SOLUBLE FIBER

[75] Inventor: Norman A. Greenberg, New Hope, Minn.

[73] Assignee: Sandoz Ltd., Basel, Switzerland

[21] Appl. No.: 878,096

[22] Filed: May 4, 1992

Related U.S. Application Data

[63] Continuation-in-part of Ser. No. 602,531, Oct. 24, 1990, abandoned.

[51] Int. Cl.$^5$ .............................................. A61K 37/02
[52] U.S. Cl. ........................................ 514/21; 426/71;
426/656; 514/782; 514/783
[58] Field of Search ............... 514/21, 782, 783; 426/656, 71

[56] References Cited
FOREIGN PATENT DOCUMENTS 9004334 5/1990 PCT Int'l Appl. .

OTHER PUBLICATIONS

Struthers, J. Nutr., vol. 116, pp. 47-49 (1986).
Gut, vol. 30, pp. 246-264 (1989).
Patil, et al., Clinical Nutrition, vol. 4, pp. 67-71 (1985).
Scheppach, et al., J. Parenteral and Enteral Nutrition, vol. 14, pp. 204-209 (1990).
Nyman, et al., British Journal of Nutrition, vol. 55, pp. 487-496 (1986).
Frankenfield, et al., Am. J. Clin. Nutr., vol. 50, pp. 533-538 (1989).
McBurney, et al., J. of Food Science, vol. 54, pp. 347-350 (1989).

*Primary Examiner*—Michael G. Wityshyn
*Assistant Examiner*—Choon P. Koh
*Attorney, Agent, or Firm*—Robert S. Honor; Melvyn M. Kassenoff; Carl W. Battle

[57] ABSTRACT

A nutritionally complete feeding composition contains soluble fiber, especially hydrolyzed guar gum or pectin. This composition provides nourishment to colon cells, preventing bacterial sepsis and also preventing diarrhea.

14 Claims, No Drawings

ENTERAL NUTRITION AND MEDICAL FOODS HAVING SOLUBLE FIBER

This application is a continuation in part of application Ser. No. 07/602,531, filed Oct. 24, 1990, now abandoned.

This application relates to low-viscosity enteral and medical foods which contain fiber, especially soluble fiber, and to the use of these foods to maintain healthy colon cells and to prevent bacterial sepsis.

Nutritionally complete liquid diets are often administered to patients either orally or through feeding tubes (enterally). It has been noted that a frequent side-effect of this type of feeding is diarrhea. Diarrhea can lead to fluid and/or electrolyte imbalance and malnutrition. Further, it can cause discomfort and sanitation problems, require considerable staff time, thus resulting in increase patient care costs.

Secondly, it has also been noted that many critically ill patients develop bacterial sepsis, a leading cause of death in intensive care units.

Feeding compositions are currently known which contain soy polysaccharide fiber. Soy polysaccharide fiber is considered to be an insoluble fiber. A recent study questioned the effectiveness of such a formulation in preventing diarrhea. See, e.g. Frankenfield et al., 1989. "Soy-Polysaccharide Fiber: Effect on Diarrhea in Tube-fed, Head Injured Patients" *Am. J. Clin. Nutr.* 50:533-538.

DESCRIPTION OF THE INVENTION

It has been found that adding a soluble fiber supplement to an otherwise nutritionally complete liquid food composition can prevent both diarrhea and bacterial sepsis while retaining the low viscosity character of the food composition. This invention, therefore relates to food compositions comprising such soluble fiber, and to the use of such food compositions to prevent both diarrhea and bacterial sepsis.

As used throughout the specification and claims, the term "nutritionally complete" refers to a feeding composition which contains carbohydrates, proteins, essential fatty acids, vitamins, and minerals in such amounts that a person can ingest only that composition for a prolonged period of time and not suffer any malnutrition. The composition may have water added to it such that the composition is in liquid form and suitable for drinking or for use with a tube-feeding apparatus. Alternatively, the composition may be in dry form.

Numerous feeding compositions are known and commercially available, including those commercially available from Sandoz Nutrition Corp. under the trademarks RESOURCE ® and ISOSOURCE ® (both liquid formulations) and STRESSTEIN ® (dry product). These compositions typically provide approximately 20-70% of calories in the form of carbohydrates, 13-30% of calories in the form of protein, 20-50% of calories as lipid (which includes essential fatty acids) as well as vitamins, minerals, and optionally water, flavoring agents, fillers, binders, coloring agents, coating materials, or other nutritional supplements.

As used throughout the specification and claims, the term "soluble fiber" refers to fibers which are able to undergo fermentation in the colon to produce short chain fatty acids (SCFA). Examples of soluble fibers are: pectin, guar, hydrolyzed guar, and gum arabic. "Insoluble fibers" are those fibers which will not go into solution. Examples of insoluble fibers include soy polysaccharides and brans.

It has been found in accordance with this invention that certain soluble fibers can be added to feeding compositions, and result in a composition which prevents diarrhea and bacterial sepsis. The soluble fiber may be the only fiber in the feeding composition, i.e. it may be added to a feeding composition which previously did not contain any fiber, or it may replace fiber which previously was present in the feeding composition. Alternatively, the soluble fiber may be an addition to an insoluble fiber present in the feeding composition.

The soluble fiber may be chosen from numerous known soluble fibers, including locust beam gum, xanthan gum, guar gum, hydrolyzed guar gum, and pectin. The preferred fibers, for numerous reasons set forth below are hydrolyzed guar gum and pectin; hydrolyzed guar gum being the most preferred.

One primary requirement, especially for enteral compositions, is that the soluble fiber should not substantially increase the viscosity of the product above approximately 50 cp, and it is preferred that the viscosity remain under 25 cp, more preferably 10-25 cp. As used throughout the specification and claims, the term "low viscosity" means a viscosity of less than 25 cp.

A particularly preferred hydrolyzed guar gum is commercially available from Taiyo Kagaku Co, Ltd. (Japan) under the trade name Sun Fiber. Sun Fiber is a purified hydrolyzed guar gum prepared by hydrolyzing guar gum with $\beta$-mannase from *Aspergillus niger*. Prior to hydrolysis, the molecular weight of guar gum is approximately 200,000; after hydrolysis it is 20,000-30,000. For use in accordance with this invention, the molecular weight range of the hydrolyzed guar gum may vary, as long as the viscosity of the finished product does not exceed 50 cp.

The amount of soluble fiber added to a feeding composition may vary depending on the needs of the patient and whether the composition is to be taken orally or enterally. Thus the fiber content of the composition may vary according to the amount of composition intended to be ingested per day. It is generally preferred that the soluble fiber content of the composition be adjusted so that the patient receives approximately 10-60 g/day soluble fiber, and more preferably approximately 20 g/day soluble fiber.

It is well known that colon cells nourished by exclusively liquid diets may atrophy. This atrophy manifests itself in a breaking down of the gut mucosal barrier, allowing gram negative bacterial and/or bacterial endotoxin produced by these bacteria to invade the patient's circulatory system, causing shock. It has been found in accordance with this invention, that providing colon cells with a source of fiber which can be fermented into butyric acid, maintains health of the colon cells and the intactness of the gut mucosal barrier, reducing the incidence of septic shock. In addition, the healthy colon cells can retain minerals better, and are able to reabsorb water. Pectin and hydrolyzed guar gum are particularly good sources of butyric acid, as detailed in Example 1, below.

Another benefit which can be realized by the addition of either hydrolyzed guar gum or pectin is that diarrhea can be controlled.

This invention is further illustrated in the following non-limiting examples.

EXAMPLE 1

Fermentability of Fibers

Various fibers are suspended in water and buffered to neutrality. A sample of microorganisms normally found in the colon is added and fermentation is allowed to occur for 24 hours at 37° C. in a mannometer. The resulting ferment is analyzed for the amount of butyric acid per gram of fiber. Results are presented below:

| Fiber | Millimoles of Butyric Acid per Gram of Fiber |
|---|---|
| Hydrolyzed Pectin | 0.38 |
| Pectin | 0.28 |
| Sun Fiber (hydrolyzed guar) | 1.45 |
| Guar | 0.86 |
| Gum Arabic | 0.22 |
| Soy Polysaccharide | 1.16 |
| Polydextrose | 0.16 |

As can be seen from the above, the hydrolysis of both pectin and guar improves the fermentability of these fibers. The results for soy polysaccharide may be misleadingly high due to a starch associated with the insoluble fiber. In a mammalian system, the soy polysaccharide could be expected to yield much less butyric acid.

EXAMPLE 2

Oral Supplement Containing Soluble Fiber

An oral supplement is made using the following ingredients.

| INGREDIENT | FORMULA PERCENTAGE |
|---|---|
| Deionized Water | 75.51 |
| Maltrin 200 (maltodextrin) | 10.47 |
| Sugar—Canners grade | 3.66 |
| Corn Oil | 3.40 |
| Sodium Caseinate | 2.97 |
| *Mineral premix | 0.38 |
| Calcium Caseinate | 0.48 |
| **Gum premix | 0.02 |
| Soy Protein isolate | 0.48 |
| ***Vitamin premix | 0.07 |
| Artificial Vanilla Flavor | 0.18 |
| Magnesium Chloride | 0.18 |
| Lecithin | 0.17 |
| Potassium Citrate | 0.26 |
| Choline Chloride | 0.07 |
| Potassium Hydroxide | 0.05 |
| Natural & Artificial Vanilla Flavor | 0.01 |
| Vitamin E Oil | 0.12 |
| Potassium Chloride | 0.10 |
| Antifoam | 0.02 |
| Soluble Fiber | 1.4 |
| | 100.00 |

*Mineral premix contains:
| | |
|---|---|
| Tricalcium phosphate | 0.20765% |
| Sodium citrate | 0.16730 |
| Zinc sulfate | 0.00538 |
| Ferrous sulfate | 0.00330 |
| Copper gluconate | 0.00100 |
| Manganese sulfate | 0.00076 |
| Potassium iodide | 0.00036 |

**Gum premix contains:
| | |
|---|---|
| Caragennan | 0.01440% |
| Carrageenan | 0.00960% |

***Vitamin premix contains:
| | |
|---|---|
| Ascorbic acid | 0.05616% |
| Niacinamide | 0.00230 |
| Biotin | 0.00197 |
| Vitamin A | 0.00178 |
| Calcium pantothenate | 0.00119 |
| Cyanocobalamin B12 | 0.00098 |
| Vitamin K | 0.00070 |
| Thiamin hydrochloride | 0.00035 |
| Pyridoxine hydrochloride | 0.00035 |
| Folic acid | 0.00029 |
| Vitamin D | 0.00028 |
| Riboflavin B2 | 0.00022 |

Oil is heated to 155°–165° F. Wet salts and gum premix is added to the deionized water which is heated to 140° F. Next, the maltrin, sugar, caseinates, and soy protein is added. The soluble fiber source is then added. The soluble fiber may be either hydrolyzed guar gum or pre-treated pectin (at least 0.25%, which equals at least 15 g per 2,000 calories). pH is adjusted to 6.8. Next, the potassium citrate and the mineral premix are added and temperature is increased to 150° F. The hot oil is then added and heated to 165° F. The mixture is then homogenized. Vitamin premix and flavor is added and mixed thoroughly. The mixture is then heat processed and packaged aseptically.

EXAMPLE 3

Replacing Insoluble Fiber with Soluble Fiber

A currently available product, FIBERSOURCE®, contains soy polysaccharide which is insoluble fiber. Hydrolyzed guar gum may be used to replace the soy polysaccharide or may be added in addition to the soy polysaccharide. Below is an example where the hydrolyzed guar gum replaces soy polysaccharide on a one-to-one basis, but other ratios may be used. If one wished to replace soy polysaccharide with hydrolyzed pectin, a different emulsifier system is needed.

| INGREDIENT | % FORMULA |
|---|---|
| Deionized water | 73.29 |
| Maltrin 100 (maltodextrin) | 11.33 |
| Maltrin 200 (maltodextrin) | 4.500 |
| Sodium Caseinate | 3.227 |
| Medium Chain Triglyceride Oil | 1.994 |
| Canola Oil | 1.779 |
| Sun Fiber | 1.319 |
| Calcium Caseinate | 1.209 |
| Potassium Citrate | 0.4050 |
| Vanilla Flavor | 0.1000 |
| Sodium Citrate | 0.2025 |
| Magnesium Chloride | 0.1829 |
| Tricalcium Phosphate | 0.1411 |
| *H₂O Vitamin premix | 0.06329 |
| Potassium Chloride | 0.08406 |
| Polyglycerol esters of fatty acids | 0.06136 |
| **Multimineral premix | 0.02859 |
| Choline Chloride | 0.04522 |
| ***Fat/Vitamin premix | 0.00288 |
| Vitamin E Oil | 0.003600 |
| Dipotassium Phosphate | 0.03283 |
| | 100.0 |

*H₂O Vitamin Premix contains:
| | |
|---|---|
| Sodium ascorbate | 0.05522% |
| Niacinamide (B₃) | 0.003280 |
| Calcium pantothenate | 0.002100 |
| Cyanocobalamin (B₁₂) | 0.001440 |
| Thiamin hydrochloride | 0.000450 |
| Pyridoxine hydrochloride | 0.000420 |
| Riboflavin (B₂) | 0.000300 |
| Biotin | 0.000050 |
| Folic acid | 0.000030 |

**Multimineral premix contains:
| | |
|---|---|
| Selenium yeast | 0.01019 |
| Chromium east | 0.005150 |
| Zinc sulfate | 0.004910 |

-continued

| Ferrous sulfate | 0.004910 |
|---|---|
| Manganese sulfate | 0.001210 |
| Sodium molybdate | 0.001100 |
| Copper gluconate | 0.001100 |
| Potassium iodide | 0.000020 |
| ***Fat/vitamin premix contains: | |
| Vitamin A palmitate | 0.001720 |
| Vitamin K | 0.000780 |
| Vitamin D$_3$ | 0.000380 |

EXAMPLE 4

Oral Supplement with Soluble Fiber

The following composition is suitable as an oral supplement. Although oral supplements are often viscous, this formulation retains a low viscosity. The addition of 1% hydrolyzed guar gum leads to a high viscosity product which, while not wishing to be bound by theory, may be due to an interaction between the protein and hydrolyzed guar gum. However, it has been found that at a somewhat lower amount of fiber, the supplement will remain its low viscosity.

| INGREDIENT | % FORMULA |
|---|---|
| Deionized Water | 76.5541 |
| Sugar | 14.5 |
| Whey Protein Concentrate | 3.88 |
| Sunflower Oil | 2.10 |
| Corn Syrup Solids | 1.17 |
| Phosphoric Acid (75%) | 0.315 |
| Citric Acid | 0.190 |
| Flavor/Color | 0.100 |
| Polyglycerol Ester | 0.050 |
| Sucrose Fatty Acid Ester | 0.050 |
| Cysteine | 0.050 |
| *Vitamin and Mineral Premix | 0.79089 |
| Soluble Fiber | 0.25 |
| | 100.00 |

| *Premix contains: | |
|---|---|
| Magnesium gluconate | 0.400 |
| Calcium chloride | 0.190 |
| Choline bitartrate | 0.121 |
| Ascorbic acid | 0.056 |
| Vitamin E acetate | 0.00542 |
| Zinc sulfate | 0.00537 |
| Ferrous sulfate | 0.003299 |
| Niacinamide | 0.002298 |
| Vitamin A palmitate | 0.001772 |
| d-Calcium pantothenate | 0.001195 |
| Cyanocobalamin | 0.000981 |
| Copper gluconate | 0.000882 |
| Manganese sulfate | 0.000759 |
| Vitamin K$_1$ | 0.000653 |
| Thiamine hydrochloride | 0.000350 |
| Pyridoxine hydrochloride | 0.000348 |
| Vitamin D | 0.000283 |
| Riboflavin | 0.000220 |
| Folic acid | 0.000032 |
| Biotin | 0.000020 |
| Potassium iodide | 0.000018 |

The emulsifier is dissolved in hot water. Protein, sugar, maltodextrin and hydrolyzed guar gum are then added. Next, oil is added, then pre-blended acids, vitamins and minerals. The mixture is heated to 160° F., and then flavors and colors are added. The mixture is then homogenized, heat processed, and packaged aseptically.

EXAMPLE 5

Effects of Dietary Soluble and Insoluble Fiber on the Intestinal Flora, Intestinal Histology and Bacterial Transaction in Mice 1. Effect on Bacteria Four groups of mice are fed either normal mouse chow, a commercially available liquid food composition (abbreviated Liq), the liquid composition supplemented with 2.5% soy fiber (Liq+S), or the liquid composition supplemented with 2.5% hydrolyzed guar gum (Liq+G). After 14 days, the type and amount of cecal bacteria are measured. Results are presented in table 5A below. "Wt" is average (n=24) weight gain in grams in 14 days. Numbers given under the bacterial columns represent the average and standard error ($\log_{10}$) of cecal bacteria per gram (n=8)

TABLE 5A

| Diet | Wt | Aerobic + facultative gram-neg. bacilli | Aerobic + facultative gram-pos. bacteria | Strict Anaerobes |
|---|---|---|---|---|
| Chow | 3.5 | 4.3 ± 0.9 | 8.0 ± 0.2 | 9.5 ± 0.1 |
| Liq. | 4.5 | 7.6 ± 0.2$^a$ | 7.8 ± 0.2 | 9.7 ± 0.2 |
| Liq + S | 4.1 | 6.6 ± 0.2$^b$ | 8.0 ± 0.2 | 9.9 ± 0.2 |
| Liq + G | 4.7 | 6.2 ± 0.4 | 8.4 ± 0.1 | 10.2 ± 0.1$^b$ |

$^a$Significantly increased compared to chow-fed mice, $P < 0.01$ by ANOVA
$^b$Significantly increased compared to chow-fed mice, $P < 0.05$ by ANOVA The table shows that the liquid diet and the liquid diet supplemented with soy fiber both significantly increased the amount of aerobic and facultative gram-negative bacteria. Gram-negative bacteria are those which can cause bacterial sepsis if they or the endotoxins produced by them translocate into the bloodstream. No such increase was observed in the liquid food supplemented with the hydrolyzed guar. The strict anaerobe count was increased with the liquid+hydrolyzed guar, but these bacteria are considered more "benign" than the aerobic gram-negative bacteria.

2. Translocation of Bacteria

Septic shock occurs after bacteria or their endotoxins enter the bloodstream. One of the first steps in this process is the translocation of cecal bacteria to the mesenteric lymph nodes (MNL). As liquid feeding tends to increase the amount of gram-negative bacteria, it is important to maintain the blood-mucosal barrier to eliminate translocation. The effect of diet on this translocation was investigated, and results are presented below in Table 5B. Each group of mice was fed chow, Liq, Liq+S, or Liq+G as described above for 14 days.

TABLE 5B

| Diet | No. of mice with viable bacteria in MLN(%) Total No. mice$^a$ | No. and identity of bacteria in the MLN of individual mice |
|---|---|---|
| Chow | 3/24 (13%) | 10 E. coli |
| | | 20 E. coli |
| | | 450 Lactobacillus sp. |
| Liq | 1/24 (4%) | 20 coagulase-negative staphylococci |
| Liq + S | 2/24 (8%) | 10 Lactobacillus sp. |
| | | 40 Enterobacter sp. |
| Liq + G | 1/24 (4%) | 20 E. coli |

$^a$Chi-square analysis indicates no significant differences between chow-fed mice and mice fed Liq, Liq + S, or Liq + G.

Thus, as shown in the table above, addition of the hydrolyzed guar fiber did not have any adverse effects on the translocation of bacteria into the MNL.

3. Effect of Diet on Bacteria in Endotoxin Lipopolysaccharide-Treated (LPS) Mice Each group of mice was fed as previously described and was given 200 μg i.p. injection of endotoxin lipopolysaccharide, the toxin which is involved in septic shock. Results are presented in Table 5C below. Abreviations and units are the same as those used in Table 5A.

TABLE 5C

| Diet | Wt. | Aerobic + facultative gram-neg. bacilli | Aerobic + facultative gram-pos. bacteria | Strict Anaerobes |
|---|---|---|---|---|
| Chow | 0.3 | 9.0 ± 0.1 | 8.4 ± 0.2 | 9.7 ± 0.2 |
| Liq | 1.8 | 9.7 ± 0.3 | 9.4 ± 0.3$^a$ | 10.2 ± 0.2 |
| Liq + S | 2.3 | 9.2 ± 0.2 | 8.7 ± 0.2 | 9.7 ± 0.2 |
| Liq + G | 1.2 | 9.1 ± 0.2 | 8.9 ± 0.2 | 10.2 ± 0.1 |

$^a$Significantly increased compared to chow-fed mice P < 0.1 by ANOVA

None of the liquid diets were seen to have an adverse effect on the intestinal flora of LPS-treated mice. As expected, number of enteric gram-negative bacteria (primarily *E. coli*) increased with the intraperitoneal LPS treatment for all treatment groups.

4. Translocation of Bacteria to MLN in LSP-Treated Mice

Mice were fed as described supra and treated with LPS as described supra. The number and identity of bacteria found in the MLN was determined. Results are presented in Table 5D, below.

TABLE 5D

| Diet | No. mice with viable bacteria in MLN(%) Total No. of mice | No. and identity of viable bacteria in MLN of individual mice |
|---|---|---|
| Chow | 14/23 (61%)$^a$ | 60 *E. coli* |
| | | 10 *E. coli* |
| | | 60 *E. coli* |
| | | 10 *P. mirabilis* + 150 Lactobacillus sp. |
| | | 10 *E. coli* |
| | | 10 *E. coli* |
| | | 30 *E. coli* |
| | | 100 *E. coli* |
| | | 10 *E. coli* |
| | | 80 *E. coli* |
| | | 60 Enterobacter sp. |
| | | 10 *E. coli* |
| | | 10 Enterobacter sp. |
| | | 20 *E. coli* |
| Liq | 21/24 (88%) | 10 *E. coli* |
| | | 20 Enterococcus sp. |
| | | 70 Enterococcus sp. |
| | | 50 Enterococcus sp. |
| | | 10 Enterobacter + 650 Enterococcus sp. |
| | | 10 Enterococcus sp. |
| | | 10 *E. coli* + 10 Enterobacter sp. |
| | | 20 Enterococcus sp. |
| | | 120 Enterococcus sp. |
| | | 90 *E. coli* |
| | | 110 *E. coli* |
| | | 20 Enterococcus sp. |
| | | 10 Lactobacillus sp. |
| | | 20 Enterococcus sp. |
| | | 30 Enterococcus sp. |
| | | 30 *E. coli* |
| | | 10 *E. coli* + 10 Enterococcus sp. |
| | | 150 Enterococcus sp. |
| | | 10 *E. coli* |
| | | 90 Enterococcus sp. |
| Liq + S | 12/24 (50%)$^b$ | 20 *E. Coli* |
| | | 10 coagulase-negative staphylococci |
| | | 40 *E. coli* |
| | | 40 *E. coli* |
| | | 110 Enterococcus sp. |
| | | 10 Lactobaccilus sp. |
| | | 10 *E. coli* |
| | | 10 *E. coli* + 70 *S. aureus* |
| | | 40 *E. coli* |
| | | 20 Enterobacter sp. |
| | | 10 *E. coli* |
| | | 10 Enterococcus sp. |
| Liq + G | 9/24 (42%)$^c$ | 10 *E. coli* |
| | | 40 *E. coli* + 30 Enterococcus sp. |
| | | 10 Enterobacter sp. |
| | | 70 *E. coli* + 20 Enterococcus sp. |
| | | 30 *E. coli* |
| | | 60 Enterobacter sp. + 130 Enterococcus sp. |
| | | 40 Enterobacter sp. + 10 Enterococcus sp. |
| | | 20 Enterobacter sp. + 60 Enterococcus sp. |
| | | 30 Enterococcus sp. |

$^a$One mouse died out of 24 mice
$^b$Significantly decreased compared to mice fed Liq, P < 0.05 by Chi-square with continuity correction.
$^c$Significantly decreased compared to mice fed Liq, P < 0.01 by Chi-square with continuity correction.

Compared to chow fed mice, Liq+S and Liq+G have an improvement in preventing the translocation of intestinal bacteria to the mesenteric lymph nodes of mice. Compared to chow-fed mice, Liq appeared to increase the incidence of bacterial translocation somewhat (P=0.08). However, the supplementation with soy or hydrolyzed guar fiber had the beneficial effect of significantly decreasing the incidence of translocation of bacteria.

What is claimed is:

1. A feeding composition which is nutritionally complete comprising hydrolyzed soluble fiber in an amount such that the daily dosage of said feeding composition provides up to 60 grams of said hydrolyzed soluble fiber per day.

2. A composition according to claim 1 which is a liquid composition.

3. A composition according to claim 2 which has a viscosity of less than 50 cp.

4. A composition according to claim 3 which has a viscosity of less than 25 cp.

5. A composition according to claim 1 wherein the soluble fiber is selected from the group consisting of hydrolyzed guar gum and pectin.

6. A composition according to claim 2 comprising hydrolyzed guar gum.

7. A composition of claim 6 wherein said hydrolyzed gear gum is prepared by hydrolyzing guar gum with β-mannase from Aspergillus.

8. A low viscosity feeding composition comprising:
   carbohydrates providing approximately 20-70% of the total calories;
   protein providing approximately 10-30% of the total calories;
   lipid containing essential fatty acids providing approximately 20-50% of the total calories;
   vitamins;
   minerals;
   water; and
   hydrolyzed soluble fiber in an amount such that the daily dosage of the feeding composition provides about 10-60 grams of hydrolyzed soluble fiber per day.

9. A composition according to claim 8 wherein the soluble fiber is hydrolyzed guar gum.

10. The feeding composition of claim 1 wherein the amount of said hydrolyzed soluble fiber is at least 0.25% by weight of said feeding composition.

11. The feeding composition of claim 10 wherein said composition is a liquid having a viscosity of less than 50 cp and said hydrolyzed soluble fiber is hydrolyzed guar gum.

12. The feeding composition of claim 10 wherein said hydrolyzed soluble fiber is selected from the group consisting of hydrolyzed guar gum and hydrolyzed pectin.

13. The feeding composition of claim 1 wherein said feeding composition provides about 10 to 60 grams of said hydrolyzed soluble fiber per day.

14. The feeding composition of claim 7 wherein said composition has a viscosity of less than 50 cp.

* * * * *

REEXAMINATION CERTIFICATE (3200th)

United States Patent [19]
Greenberg

[11] B1 5,260,279
[45] Certificate Issued May 20, 1997

[54] NUTRITIONAL COMPOSITION COMPRISING HYDROLYZED GUAR GUM

[75] Inventor: Norman A. Greenberg, New Hope, Minn.

[73] Assignee: Sandoz Ltd., Basel, Switzerland

Reexamination Request:
No. 90/004,021, Nov. 16, 1995

Reexamination Certificate for:
Patent No.: 5,260,279
Issued: Nov. 9, 1993
Appl. No.: 878,096
Filed: May 4, 1992

Related U.S. Application Data

[63] Continuation-in-part of Ser. No. 602,531, Oct. 24, 1990, abandoned.

[51] Int. Cl.$^6$ .......... A61K 38/00; A61K 31/715
[52] U.S. Cl. .......... 514/21; 514/54; 514/782; 514/783; 536/114; 536/123.1; 426/71; 426/656
[58] Field of Search ............ 514/54, 21, 782, 514/783; 536/114, 123.1; 426/71, 656

[56] References Cited

U.S. PATENT DOCUMENTS

| | | |
|---|---|---|
| 4,971,814 | 11/1990 | Tomita ......................... 426/52 |
| 4,996,063 | 2/1991 | Inglett ......................... 426/21 |
| 5,366,755 | 11/1994 | Timonen ....................... 426/658 |

FOREIGN PATENT DOCUMENTS

| | | |
|---|---|---|
| 449594 | 10/1991 | European Pat. Off. . |
| 457098 | 11/1991 | European Pat. Off. . |
| 63-269993 | 11/1988 | Japan . |
| 64-20063 | 1/1989 | Japan . |
| 2-229117 | 9/1990 | Japan . |
| 2-248401 | 10/1990 | Japan . |
| 2201875 | 9/1988 | United Kingdom . |
| PCT WO91/ 15517 | 10/1991 | WIPO . |

OTHER PUBLICATIONS

Baker's Digest, vol. 58, No. 4, pp. 32, 33 (1984).

Patent Abstracts of Japan, vol. 15, No. 385 (1991).

*Primary Examiner*—Kathleen Kahler Fonda

[57] ABSTRACT

A nutritionally complete feeding composition contains soluble fiber, especially hydrolyzed guar gum or pectin. This composition provides nourishment to colon cells, preventing bacterial sepsis and also preventing diarrhea.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 3, 5, 6, 9, 11, 12 and 14 are cancelled.

Claims 1, 4, 7, 8, 10 and 13 are determined to be patentable as amended.

1. A [feeding] *liquid* composition which *has a viscosity of less than 50 cp and* is nutritionally complete comprising hydrolyzed [soluble fiber] *guar gum* in an amount such that the daily dosage of said [feeding] composition provides up to 60 grams of said hydrolyzed [soluble fiber] *guar gum* per day.

4. A composition according to claim [3] *1* which has a viscosity of less than 25 cp.

7. A composition of claim [6] *1* wherein said hydrolyzed guar gum is prepared by hydrolyzing guar gum with β-mannase from Aspergillus.

8. A low viscosity feeding composition *having a viscosity less than 50 cp* comprising: carbohydrates providing approximately 20–70% of the total calories; protein providing approximately 10–30% of the total calories; lipid containing essential fatty acids providing approximately 20–50% of the total calories;
vitamins;
minerals;
water; and hydrolyzed [soluble fiber] *guar gum* in an amount such that the daily dosage of the feeding composition provides about 10–60 grams of hydrolyzed [soluble fiber] *guar gum* per day.

10. The [feeding] *liquid* composition of claim 1 wherein the amount of said hydrolyzed [soluble fiber] *guar gum* is at least 0.25% by weight of said [feeding] composition.

13. The [feeding] *liquid* composition of claim 1 wherein said [feeding] composition provides about 10 to 60 grams of said hydrolyzed [soluble fiber] *guar gum* per day.

* * * * *